(12) United States Patent
Matsubara et al.

(10) Patent No.: US 9,556,183 B2
(45) Date of Patent: Jan. 31, 2017

(54) SUBSTITUTED PYRAZOLYLPYRAZOLE DERIVATIVE AND USE OF SAME AS HERBICIDE

(71) Applicant: KYOYU AGRI CO., LTD., Kanagawa (JP)

(72) Inventors: Ken Matsubara, Nagano (JP); Makoto Niino, Nagano (JP)

(73) Assignee: KYOYU AGRI CO., LTD., Kanagawa (JP)

( * ) Notice: Subject to any disclaimer, the term of this patent is extended or adjusted under 35 U.S.C. 154(b) by 0 days.

(21) Appl. No.: 14/905,007

(22) PCT Filed: Aug. 7, 2014

(86) PCT No.: PCT/JP2014/070911
§ 371 (c)(1),
(2) Date: Jan. 14, 2016

(87) PCT Pub. No.: WO2015/020156
PCT Pub. Date: Feb. 12, 2015

(65) Prior Publication Data
US 2016/0152622 A1    Jun. 2, 2016

(30) Foreign Application Priority Data
Aug. 9, 2013    (JP) .................................. 2013-167031

(51) Int. Cl.
| C07D 487/04 | (2006.01) |
| C07D 471/04 | (2006.01) |
| A01N 43/90 | (2006.01) |
| A01N 43/56 | (2006.01) |

(52) U.S. Cl.
CPC ............. *C07D 487/04* (2013.01); *A01N 43/56* (2013.01); *A01N 43/90* (2013.01); *C07D 471/04* (2013.01)

(58) Field of Classification Search
None
See application file for complete search history.

(56) References Cited

U.S. PATENT DOCUMENTS

| 5,580,986 A | 12/1996 | Dorfmeister et al. |
| 5,756,424 A | 5/1998 | Dorfmeister et al. |
| 5,869,686 A | 2/1999 | Dorfmeister et al. |

FOREIGN PATENT DOCUMENTS

| JP | 2000-515142 | 11/2000 |
| JP | 3770403 | 4/2006 |
| WO | 94/08999 | 4/1994 |
| WO | 98/03506 | 1/1998 |

OTHER PUBLICATIONS

Masuji Miyahara, Suiden Zasso no Seitai to Sono Bojo—Suitosaku no Zasso to Josozai Kaisetsu (Ecology of Paddy Weeds and their Control—Explanation of Weeds of Rice Paddy Crops and Herbicide), Dec. 15, 1992, pp. 159 (partial English translation).
International Search Report issued Sep. 9, 2014 in International Application No. PCT/JP2014/070911.

*Primary Examiner* — Kamal Saeed
(74) *Attorney, Agent, or Firm* — Wenderoth, Lind & Ponack, L.L.P.

(57) ABSTRACT

Provided is a compound capable of effectively control worst weeds of higher leaf stages that present practical problems. A specific pyrazolylpyrazole derivative of formula (I) is disclosed that is able to solve the above-mentioned problems.

(I)

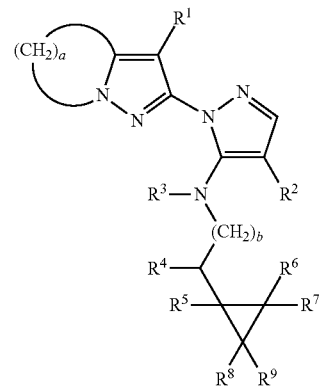

11 Claims, No Drawings

SUBSTITUTED PYRAZOLYLPYRAZOLE DERIVATIVE AND USE OF SAME AS HERBICIDE

TECHNICAL FIELD

The present invention relates to a substituted pyrazolylpyrazole derivative and the use of that compound as an herbicide.

BACKGROUND ART

Numerous herbicides have recently come to be used in the cultivation of agricultural crops, and have contributed to reduced labor for farmers and improved productivity of agricultural crops. Numerous herbicides are also used practically in the cultivation of field and paddy rice.

However, there is considerable diversity in the species of weeds, the germination and growth periods of each species of weed are not uniform, and the growth of perennial weeds extends over a long period of time. Consequently, it is extremely difficult to control all weeds with a single spraying of herbicide.

Early to mid-term one-shot herbicides have been shown to be effective for paddy rice by treating during the second to third leaf stage of paddy weeds (generic term for *Echinochloa oryzicola, Echinochloa crus-galli* var. *crus-galli, Echinochloa crus-galli* var. *formosensis, Echinochloa crus galli* var. *praticola* and *Echinochloa crus-galli* var. *caudata*), and major weeds can be controlled by a single treatment (see Non-Patent Document 1). However, it is extremely difficult to control paddy weeds that have grown to the 3.5 leaf stage or more with early to mid-term one-shot herbicides currently in practical use, and the control of paddy weeds in the third leaf stage and control of paddy weeds in the 3.5 leaf stage are technically completely different.

Moreover, maintaining herbicidal effects (or residual activities) over a long period of time is important in terms of reducing spraying of agricultural chemicals, saving on labor and curtailing costs, and is considered to be an essential area of performance for early to mid-term one-shot herbicides.

In addition, acetolactate synthase (ALS) inhibitors have come to be widely used in recent years, and weeds exhibiting resistance to ALS inhibitors have become a problem. There are few herbicides demonstrating adequate efficacy against ALS inhibitor-resistant biotypes of the perennials of *Sagittaria trifolia* and *Sagittaria pygmeae*. In addition, examples of perennial weeds that have caused problems in recent years include *Eleocharis kuroguwai, Scirpus planiculmis* and *Scirpus nipponicus*, while examples of annuals include *Aeschynomene indica, Leptochloa chinensis* and *Murdannia keisak*, and there are few herbicides that demonstrate adequate efficacy against these difficult-to-control weeds.

On the other hand, numerous pyrazole derivatives are used practically as herbicides, and although pyrazole derivatives such as 4-(2,4-dichlorobenzoyl)-1,3-dimethyl-5-pyrazolyl p-toluenesulfonate (common name: "Pyrazolate"), 2-[4-(2,4-dichlorobenzoyl)-1,3-dimethylpyrazol-5-yloxy] acetophenone (common name: "Pyrazoxyfen") or 2-[4-(2, 4-dichloro-m-toluoyl)-1,3-dimethylpyrazol-5-yloxy]-4'-methylac etophenone (common name: "Benzofenap") are widely used, their registered application range for paddy weeds in Japan when used alone is up to the 1.5 leaf stage, and although these pyrazole derivatives are effective against a wide range of weeds, the efficacy thereof is not always adequate against paddy weeds of higher leaf stages.

In addition, although Compound 73 of Example 4 described in WO 94/08999 in the form of 1-(3-chloro-4,5, 6,7-tetrahydropyrazolo[1,5-a]pyridin-2-yl)-5-[methyl(prop-2-ynyl)amino]pyrazole-4-carbonitrile (common name: "Pyraclonil") is effective against a wide range of weeds, its efficacy against paddy weeds of higher leaf stages is inadequate, and the registered application range in Japan against paddy weeds when using this herbicide alone is up to the 1.5 leaf stage.

CITATION LIST

Patent Literature Document

Patent Document 1: WO 94/08999

Non-Patent Literature Document

Non-Patent Document 1: "Suiden Zasso no Seitai to Sono Bojo—Suitosaku no Zasso to Josozai Kaisetsu (Ecology of Paddy Weeds and their Control—Explanation of Weeds of Rice Paddy Crops and Herbicide)", p. 159

SUMMARY OF THE INVENTION

Technical Problem

An object of the present invention is to provide a herbicide composition that has a wide herbicidal spectrum, is able to control worst weeds of higher leaf stages that present practical problems, and not cause phytotoxicity to crops such as paddy rice.

Solution to Problem

As a result of conducting extensive studies to achieve the aforementioned object, the inventors of the present invention found that a pyrazolylpyrazole derivative having a specific chemical structure exhibits a wide herbicidal spectrum over a long period of time, demonstrates superior herbicidal efficacy against worst weeds of higher leaf stages, and has adequate safety with respect to cultivated crops, thereby leading to completion of the present invention on the basis of these findings. Thus, the present invention provides a pyrazolylpyrazole derivative in the form of a compound represented by the following formula (I):

[Chemical formula 1]

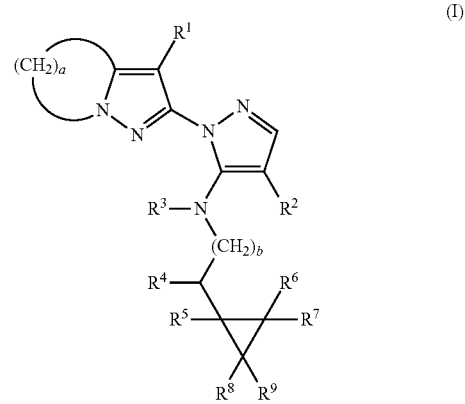

In the above formula, $R^1$ represents a halogen atom, $R^2$ represents a cyano group, nitro group or halogen atom, $R^3$ represents a hydrogen atom, trifluoroacetyl group, pentafluoropropionyl group or heptafluorobutenyl group, $R^4$-$R^9$ may be the same or different and represent hydrogen atoms, halogen atoms, $C_1$-$C_6$ alkyl groups (which may be substituted with one or more halogen atoms depending on the case), $C_3$-$C_6$ cycloalkyl groups (which may be substituted with one or more halogen atoms depending on the case), $C_2$-$C_6$ alkenyl groups (which may be substituted with one or more halogen atoms depending on the case), $C_2$-$C_6$ alkynyl groups (which may be substituted with one or more halogen atoms depending on the case), $C_1$-$C_6$ alkoxy($C_1$-$C_6$)alkyl groups (which may be substituted with one or more halogen atoms depending on the case), or phenyl groups (which may be substituted with one or more halogen atoms, nitro groups, cyano groups, $C_1$-$C_4$ alkyl groups (which may be substituted with one or more halogen atoms depending on the case) or $C_1$-$C_4$ alkoxy groups depending on the case), a represents 3 to 5, and b represents 0 to 2.

Preferably, in formula (I), $R^1$ represents a chlorine atom or bromine atom, $R^4$-$R^9$ may be the same or different and represent hydrogen atoms, halogen atoms, $C_1$-$C_4$ alkyl groups (which may be substituted with one or more halogen atoms depending on the case), $C_3$-$C_6$ cycloalkyl groups (which may be substituted with one or more halogen atoms depending on the case), $C_2$-$C_4$ alkenyl groups (which may be substituted with one or more halogen atoms depending on the case), $C_2$-$C_4$ alkynyl groups (which may be substituted with one or more halogen atoms depending on the case), $C_1$-$C_4$ alkoxy($C_2$-$C_4$)alkyl groups (which may be substituted with one or more halogen atoms depending on the case), or phenyl groups (which may be substituted with one or more halogen atoms, nitro groups, cyano groups, $C_1$-$C_4$ alkyl groups (which may be substituted with one or more halogen atoms depending on the case) or $C_1$-$C_4$ alkoxy groups depending on the case), and a represents 4.

In the present description, a description in the manner of the previous "$C_a$-$C_b$" of each substituent refers to the number of carbon atoms respectively present in that group being from a to b.

Fluorine atoms, chlorine atoms, bromine atoms and iodine atoms are included in "halogen atoms".

"Alkyl" as referring to a group per se or a moiety of a group can be linear or branched, and although there are no limitations thereon, examples thereof include methyl, ethyl, n- or iso-propyl, n-, iso-, sec- or tert-butyl, n-pentyl and n-hexyl groups, and each is selected within a range of the specified number of carbon atoms thereof.

An "alkoxy group" refers to an alkyl-O-group in which the alkyl moiety has the above-mentioned meaning, and although there are no limitations thereon, examples thereof include methoxy, ethoxy, n- or iso-propoxy, n-, iso-, sec- or tert-butoxy groups, and each is selected within a range of the specified number of carbon atoms thereof.

Although there are no limitations on "cycloalkyl group", examples thereof include cyclopropyl, cyclobutyl, cyclopentyl and cyclohexyl groups, and each is selected within a range of the specified number of carbon atoms thereof.

An "alkenyl group" refers to an unsaturated hydrocarbon group that is linear or branched and has one or two or more double bonds in a molecule thereof, and although there are no limitations thereon, specific examples thereof include a vinyl group, 1-propenyl group, 2-propenyl group, 2-butenyl group, 2-methyl-2-propenylgroup, 3-methyl-2-butenyl group and 1,1-dimethyl-2-propenyl group, and each is selected within a range of the specified number of carbon atoms thereof.

An "alkynyl group" refers to an unsaturated hydrocarbon group that is linear or branched and has one or two or more triple bonds in a molecule thereof, and although there are no limitations thereon, specific examples thereof include an ethynyl group, 1-propynyl group, 2-propynyl group, 1-butynyl group, 2-butynyl group, 3-butynyl group and 1,1-dimethyl-2-propynyl group, and each is selected within a range of the specified number of carbon atoms thereof.

In the case of the "alkyl group", "cycloalkyl group", "alkenyl group", "alkynyl group" and "alkoxy group", at least one hydrogen atom contained in these groups may be substituted with a halogen atom, and although there are no limitations thereon, examples thereof when using the example of an alkyl group include chloromethyl, dichloromethyl, trifluoromethyl, chloroethyl, dichloroethyl, trifluoroethyl, tetrafluoropropyl, bromoethyl, bromopropyl, chlorobutyl, chlorohexyl and perfluorohexyl groups, and each of these is selected within a range of the specified number of carbon atoms thereof.

In the case where the aforementioned group or moiety is substituted with a plurality of halogen atoms or a phenyl group is substituted with a plurality of halogen atoms, nitro groups, cyano groups, $C_1$-$C_4$ alkyl groups (which may be substituted with one or more halogen atoms depending on the case) or $C_1$-$C_4$ alkoxy groups, that group can be substituted with more than one halogen atoms and/or substituents that are the same or different.

The compound of formula (I) can have stereoisomers corresponding to the type and bonding form of substituents. For example, if one or more asymmetrically substituted carbon atoms are present, these stereoisomers can be enantiomers and diastereomers. Stereoisomers can be obtained from a mixture obtained during production by a commonly used separation method such as a chromatographic separation step. Stereoisomers can be produced by the use of a stereoselective reaction, the use of an optically active starting material and/or the use of an assistant. The present invention also relates to all stereoisomers and mixtures thereof which are included in the compound represented by formula (I) but are not specifically defined.

In all of the formulas listed below, substituents and symbols have the same meanings as defined for formula (I) unless specifically defined otherwise. The compound of formula (I) provided by the present invention can be produced from a compound represented by formula (II):

[Chemical formula 2]

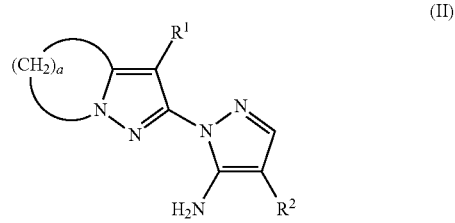

according to the following synthesis methods (A), (B) or (C), or by a synthesis method (D) following either of synthesis methods (A), (B) or (C)

Synthesis Method (A):

This is a synthesis method for a compound of formula (I) comprising the reaction of a compound of the above-mentioned formula (II) with a compound represented by the following formula (III):

[Chemical formula 3]

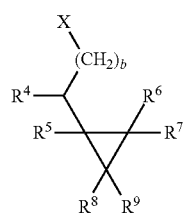

(III)

(wherein,

X represents a halogen atom, tosylate or mesylate) in the presence of a base.

Synthesis Method (B):

This is a synthesis method for a compound of formula (I) comprising dehydration and condensation a compound of the aforementioned formula (II) with a compound represented by the following formula (IV):

[Chemical formula 4]

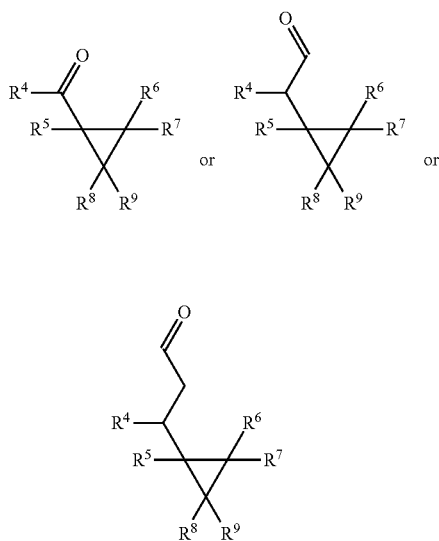

(IV)

to form a Schiff base followed by reacting with a reducing agent.

Synthesis Method (C):

This is a synthesis method for a compound of formula (I) comprising the reaction of a compound of the above-mentioned formula (II) with a compound represented by the following formula (V):

[Chemical formula 5]

(V)

(wherein,

Y represents a hydroxyl group, alkoxy group or halogen atom) to form an amide followed by halogenation and reaction with a reducing agent.

Synthesis Method (D):

This is a synthesis method for a compound of formula (I) comprising carrying out a perfluoroamidation reaction after having carried out any of production methods (A), (B) and (C) in the case where $R^3$ in the compound of formula (I) does not contain a hydrogen atom.

The compound of formula (II) used in any of production methods (A), (B) and (C) can be synthesized from tetrahydro-2H-pyran-2-ylideneacetonitrile or 5-chlorovaleryl chloride in accordance with the methods described in WO 93/10100 and WO 94/08999.

The compound of formula (III) used as another starting material in production method (A) can be a known compound per se or can be synthesized in the same manner as known compounds (see, for example, Japanese Patent Application Laid-open No. 2011-173838, Japanese Translation of PCT Application No. 2000-504733, J. Org. Chem. 1984, 49, 431-435, and Japanese Translation of PCT Application No. 2011-506349).

The reaction between the compound of (II) and the compound of (III) can be carried out by referring to known reaction conditions (see, for example, WO 94/08999).

With respect to the base used when carrying out the reaction, the reaction can be preferably carried out in the presence of at least one equivalent of a suitable base, and depending on the case, in the presence of a suitable solvent. The base may be an inorganic base such as an alkaline metal carbonate, hydroxide or metal hydride, or an organic base such as a tertiary amine or metal alkoxide. Examples of suitable inorganic bases include sodium carbonate, sodium hydroxide, potassium hydroxide and sodium hydride, while examples of suitable organic bases include trialkylamines, such as trimethylamine or triethylamine, and pyridine or other amine bases such as 4-N,N-dimethylaminopyridine, N,N-dimethylaniline, 1,4-diazabicyclo[2,2,2]octane or 1,8-diazabicyclo[5.4.0]undec-7-ene. These can normally be used within a range of 0.01 moles to 5 moles with respect to the compound of formula (II).

Examples of the solvent include ethers such as diethyl ether, tetrahydrofuran or dioxane, dipolar aprotic solvents such as N,N-dimethylformamide or dimethylsulfoxide, aromatic hydrocarbons such as benzene, toluene or xylene, nitriles such as acetonitrile, and mixed solvents thereof.

In addition, a catalyst can also be used as necessary, and examples of such catalysts include, but are not limited to, quaternary ammonium salts such as tetramethyl ammonium chloride, tetramethyl ammonium bromide, tetraethyl ammonium chloride, tetraethyl ammonium bromide, tetrabutyl ammonium chloride, tetrabutyl ammonium bromide, trimethylbenzyl ammonium chloride, trimethylbenzyl ammonium bromide, triethylbenzyl ammonium chloride, triethylbenzyl ammonium bromide, cetyltrimethyl ammonium chloride, trioctylmethylbenzyl ammonium chloride, tetrabutyl ammonium hydrogen sulfate, tetraethyl ammonium, p-toluenesulfonate, tetrapropyl ammonium hydroxide or trimethylbenzyl ammonium hydroxide, and crown ethers such as 5-crown-5, 18-crown-6, benzo-15-crown-5, dibenzo-18-crown-6 or dicyclohexano-18-crown-6.

In general, although there are no particular limitations thereon, the ratio at which the compound of formula (III) is used with respect to the compound of formula (II) is preferably such that the compound of formula (III) is within the range of 0.5 moles to 2 moles, and particularly preferably within the range of 1 mole to 1.2 moles, with respect to 1 mole of the compound of formula (II).

Although varying according to the type of starting material used, the type of catalyst and the like, the reaction temperature is normally equal to or lower than the boiling point of the solvent used, and preferably can be made to be within the range of 0° C. to 110° C.

Although varying according to the type of starting material and the reaction conditions, the reaction time is normally about 0.5 hours to 72 hours.

The compound of formula (IV) used as another starting material in production method (B) is commercially available or can be easily produced according to a known production method described in the literature (for example, Japanese Patent Application Laid-open No. 2012-180338) and literature cited therein.

Suitable conditions for forming the Schiff base used when condensing the compound of (II) and the compound of (IV) are dependent on the properties of the starting materials and the compound formed, namely properties such as solubility, reactivity or stability. Although these types of conditions are required to be selected individually, production can be easily carried out according to a known condensation method described in the literature (for example, Japanese Patent Application Laid-open No. Hei 5-148240) and literature cited therein.

There are no particular limitations on acid used provided it is a Brønsted acid or Lewis acid. For example, sulfuric acid, hydrochloric acid or p-toluenesulfonic acid can be used preferably. Examples include solid acids such as acid-type ion exchange resins, acidic clay or heteropolyacids, and/or water removers such as sodium sulfate (or magnesium sulfate) or molecular sieves. Although there are no particularly limitations on the amount of acid, it is equal to or less than the stoichiometric amount of the carbonyl compound, primary amine compound and secondary amine compound used. Moreover, reaction water can also be removed from the reaction mixture by azeotropic distillation in order to accelerate the reaction as necessary.

Examples of solvents include ethers such as diethyl ether, tetrahydrofuran or dioxane, dipolar aprotic solvents such as N,N-dimethylformamide or dimethylsulfoxide, aromatic hydrocarbons such as toluene or xylene, nitriles such as acetonitrile, halogenated hydrocarbons such as chloroform, carbon tetrachloride or dichloromethane, and mixed solvents thereof.

The solvent used when reducing the Schiff base is only required to be that which does not significantly impair the reaction, and examples thereof include ethers such as diethyl ether, dioxane or tetrahydrofuran (THF), and alcohols such as methanol, ethanol, propanol or 2-propanol. There are no particular limitations on the reducing agent, and an ordinary reducing agent can be used. Specific examples thereof include borane THF complex, sodium borohydride, sodium cyanoborohydride, lithium borohydride and lithium aluminum hydride, and among these, sodium borohydride is particularly preferable. Although the amount of the reducing agent used is only required to be 1 equivalent or more with respect to the Schiff base, it is preferably within the range of 1.5 equivalents to 100 equivalents and more preferably within the range of 1.5 equivalents to 10 equivalents. There are no particular limitations on the method used to add the reducing agent, and the reducing agent may or may not be dissolved in a solvent, and may be added all at once or added a little at a time. Addition of the reducing agent can be carried out in inert gas atmosphere such as a nitrogen or argon atmosphere as desired. The reaction temperature is selected from within the range of −20° C. to 120° C., and is preferably within the range of 0° C. to room temperature. Although varying according to the reaction scale, reaction temperature and the like, the reaction time is within the range of 1 hour to 24 hours, and purification can be carried out by isolating in accordance with ordinary methods followed by a method such as crystallization, distillation or column chromatography and the like as necessary.

In addition, in the reaction between the compound of formula (II) and the compound of formula (IV), a reductive amidation reaction may be used that allows the compound formula (I) to be synthesized in a single step. The compound of formula (I) can be easily produced according to a known method described in the literature (such as J. Org. Chem., 1996, 61, 3849-3862, J. Am. Chem. Soc., 1971, 93, 2897 or Tetrahedron, 2004, 60, 7899) and in the literature cited therein.

The compound of formula (V) used as another starting material in synthesis method (C) is either commercially available or can be produced using an inherently known method (such as Japanese Translation of PCT Application No. 2003-509403).

The amide compound formed by the reaction between the compound of formula (II) and the compound of formula (IV) in synthesis method (C) can be synthesized under the conditions indicated below. In a condensation reaction between a carboxylic acid and amine, the amide compound can be synthesized according to, for example, Org. Synth., 1, 82 (1941) or Japanese Patent Application Laid-open No. Sho 61-15867, in a reaction between an acid chloride and an amine, the amide compound can be synthesized according to, for example, Japanese Patent Application Laid-open No. Sho 61-15867, and in a reaction between an ester and an amine, the amide compound can be synthesized according to, for example, J. Org. Chem., 1963, 28, 2915.

Methods for halogenating the formed amide compound and subsequently reacting with a reducing agent can be carried out using a known method (see, for example, Japanese Patent Application Laid-open No. 2001-72676).

The perfluoroamidation reaction of production method (D) can be easily carried out under known reaction conditions and a known method described in the literature cited therein (see, for example, Japanese Patent Application Laid-open No. 2005-154420).

The compound of formula (I) provided by the present invention has superior herbicidal efficacy and is useful as a herbicide as is clear from the results of the herbicidal activity tests described in Test Examples 1 to 3 to be subsequently described.

The compound of formula (I) of the present invention has activity against numerous types of crop weeds and non-crop weeds. Examples of cultivated plants include gramineous plants such as rice, wheat, barley, corn, oats or *sorghum*, broadleaf crops such as soybeans, cotton, beets, sunflowers or rapeseed, fruit trees, vegetables such as fruit vegetables, root vegetables or leafy vegetables, and grasses, and the compound of formula (I) can be used for the cultivation thereof.

The compound of the present invention has herbicidal efficacy against the various weeds listed below that cause problems in rice paddies in any of the treatment methods of soil treatment in an irrigated or unirrigated state, soil incorporation treatment and foliar treatment. Although the following lists examples thereof, these weeds are not limited to the following examples.

Examples of paddy weeds that can be controlled by the compound of formula (I) of the present invention include Alismataceous weeds such as *Alisma canaliculatum, Sagittaria trifolia* or *Sagittaria pygmaea*, Cyperaceous weeds such as *Cyperus difformis, Cyperus serotinus, Scirpus juncoides, Eleocharis kuroguwai, Scirpus planiculmis* or *Scirpus nipponicus*, Scrophulariaceous weeds such as *Lindernia procumbens, Lindernia dubia* subsp. *dubia* or *Lindernia dubia*, Pontederiaceous weeds such as *Monochoria vaginalis* or *Monochoria korsakowii*, Potamogetonaceous weeds such as *Potamogeton distinctus*, Lythraceous weeds such as *Rotala indica* or *Ammannia multiflora*, Asteraceous weeds such as *Bidens tripartita* or *Bidens frondosa*, Leguminoseous weeds such as *Aeschynomene indica*, Commelinaceous weeds such as *Murdannia keisak*, and Gramineous weeds such as *Echinochloa oryzicola, Echinochloa crus-galli* var. *crus-galli, Echinochloa crus-galli* var. *formosensis, Echinochloa crus-galli* var. *praticola, Echinochloa crus-galli* var. *caudata, Leptochloa chinensis, Leersia japonica, Paspalum distichum* or *Leersia oryzoides*.

In addition, the compound of the present invention has herbicidal efficacy against the various weeds listed below that cause problems in field land and non-crop land in any of the treatment methods of soil treatment, soil incorporation treatment and foliar treatment. Although the following lists examples thereof, these weeds are not limited to the following examples.

Examples thereof include broadleaf weeds, including Solanaceous weeds such as *Solanum nigrum* or *Datura stramonium*, Malvaceous weeds such as *Abutilon avicennae* or *Sida spinosa*, Convolvulaceous weeds such as *Ipomoea pupurea*, Amaranthaceous weeds such as *Amaranthus lividus*, Asteraceous weeds such as *Xanthium strumarium, Ambrosia artemisiifolia, Galinsoga ciliata, Cirsium arvense, Senecio vulgaris* or *Stenactis annuus*, Brassicaceous weeds such as *Rorippa indica, Sinapis arvensis* or *Capsella bursa-pastoris*, Polygonaceous weeds such as *Persicaria longiseta* or *Fallopia convolvulus*, Portulacaceous weeds such as *Portulaca oleracea*, Chenopodiaceous weeds such as *Chenopodium album, Chenopodium ficifolium* or *Kochia scoparia*, Caryophyllaceous weeds such as *Stellaria media*, Scrophulariaceous weeds such as *Veronica persica*, Commelinaceous weeds such as *Commelina communis*, Lamiaceous weeds such as *Lamium amplexicaule* or *Lamium purpureum*, Euphorbiaceous weeds such as *Euphorbia supina* or *Euphorbia maculata*, Rubiaceous weeds such as *Galium spurium, Galium spurium* var. *Echinospermon* or *Rubia argyi*, Violaceous weeds such as *Viola mandshurica*, and Leguminoseous weeds such as *Sesbania exaltata* or *Cassia obfusitolia*, and Gramineous weeds such as *Sorghum bicolor, Panicum dichotomiflorum, Sorghum halepense, Echinochloa crus-galli* var. *crus-galli, Digitaria ciliaris, Avena fatua, Eleusine indica, Setaria viridis, Alopecurus aequalis* or *Poa annua*, and Cyperaceous weeds such as *Cyperus rotundus*.

Moreover, the compound of the present invention is also able to control a wide range of weeds growing in mowed swaths, fallow land, orchards, grasslands, lawn grass plots, train line caps, vacant land and forest land, or on farm roads, causeways and other non-crop land.

Moreover, the compound of formula (I) of the present invention does not demonstrate phytotoxicity that becomes a problem for paddy rice in the case of any cultivation method such as direct seeding cultivation or transplantation cultivation of paddy rice.

The compound of formula (I) of the present invention can be applied before or after plant germination and can be mixed into soil before seeding.

Although the dosage of the compound of formula (I) of the present invention can be varied over a wide range corresponding to the type of compound, type of target plant, application window, location of application, properties of desired effects and the like, and as a general reference thereof, the dosage can be within the range of about 0.01 g to 100 g, and preferably about 0.1 g to 10 g, as the amount of active compound per are.

Although the compound of formula (I) of the present invention can be used alone, a formulation assistant and the like is normally incorporated in the compound of formula (I) in accordance with ordinary methods, and although there are no limitations thereon, it is preferably formulated and used in any arbitrary drug form such as a dustable powder, emulsifiable concentrate, oil miscible liquid, solubilizing agent, suspo-emulsion, fine granule, aerosol spray, less drifting dust, micro granule fine, fine grains F, granules, wettable powder, water dispersible granules, flowable concentrate, throw-in types (Jumbo), tablets, paste, emulsion in oil, water soluble powder, water soluble granule, soluble concentration or capsule suspension.

There are no limitations on formulation assistants able to be used for formulation, and examples include solid vehicles, liquid vehicles, binders, thickeners, surfactants, anti-freezing agents and preservatives.

Examples of solid vehicles include, but are not limited to, talc, bentonite, montmorillonite, clay, kaolin, calcium carbonate, sodium carbonate, sodium bicarbonate, mirabilite, zeolite, starch, acidic clay, diatomaceous earth, chaoite, vermiculite, slaked lime, vegetable powder, alumina, activated carbon, sugars, hollow glass, silica sand, ammonium sulfate and urea.

Examples of liquid vehicles include, but are not limited to, hydrocarbons (such as kerosene or mineral oil), aromatic hydrocarbons (such as toluene, xylene, dimethyl naphthalene or phenyl xylyl ethane), chlorinated hydrocarbons (such as chloroform or carbon tetrachloride), ethers (such as dioxane or tetrahydrofuran), ketones (such as acetone, cyclohexanone or isophorone), esters (such as ethyl acetate, ethylene glycol acetate or dibutyl maleate), alcohols (such as methanol, n-hexanol or ethylene glycol), polar solvents (such as N,N-dimethylformamide, dimethylsulfoxide or N-methylpyrrolidone) and water.

Examples of binders and thickeners include, but are not limited to, dextrin, sodium salts of carboxymethyl cellulose, polycarboxylic acid-based polymer compounds, polyvinylpyrrolidone, polyvinyl alcohol, sodium lignin sulfonate, calcium lignin sulfonate, sodium polyacrylate, gum arabic, sodium alginate, mannitol, sorbitol, bentonite-based mineral matter, polyacrylic acid and derivatives thereof, chaoite and natural sugar derivatives (such as xanthan gum or guar gum).

Examples of surfactants include, but are not limited to, anionic surfactants such as fatty acid salts, benzoates, alkylsulfosuccinates, dialkylsulfosuccinates, polycarboxylates, alkyl sulfate ester salts, alkyl sulfates, alkyl aryl sulfates, alkyl diglycol ether sulfates, alcohol sulfate ester salts, alkyl sulfonates, alkyl aryl sulfonates, aryl sulfonates, lignin sulfonates, alkyl diphenyl ether disulfonates, polystyrene sulfonates, alkyl phosphate ester salts, alkyl aryl phosphates, styryl aryl phosphates, polyoxyethylene alkyl ether sulfate ester salts, polyoxyethylene alkyl aryl ether sulfates, polyoxyethylene alkyl aryl ether sulfate ester salts, polyoxyethylene alkyl ether phosphates, polyoxyethylene alkyl aryl phosphate ester salts or salts of naphthalene sulfonate-formalin condensates, and nonionic surfactants such as sorbitan fatty acid esters, glycerin fatty acid esters, fatty acid polyglycerides, fatty acid alcohol polyglycol ethers, acetylene glycol, acetylene alcohol, oxyalkylene block polymers, polyoxyethylene alkyl ethers, polyoxyethylene alkyl aryl ethers, polyoxyethylene styryl aryl ethers, polyoxyethylene glycol alkyl ethers, polyoxyethylene fatty acid esters, polyoxyethylene sorbitan fatty acid esters, polyoxyethylene glycerin fatty acid esters, polyoxyethylene hydrogenated castor oil or polyoxypropylene fatty acid esters.

Examples of anti-freezing agents include, but are not limited to, ethylene glycol, diethylene glycol, propylene glycol and glycerin.

Examples of preservatives include, but are not limited to, benzoic acid, sodium benzoate, methyl paraoxybenzoate, butyl paraoxybenzoate, isopropyl methyl phenol, benzalkonium chloride, chlorhexidine hydrochloride, aqueous hydrogen peroxide, chlorhexidine gluconate, salicylic acid, sodium salicylate, zinc pyrithione, sorbic acid, potassium sorbate, dehydroacetic acid, sodium dehydroacetate, phenoxyethanol, isothiazoline derivatives such as 5-chloro-2-methyl-4-isothiazolin-3-one or 2-methyl-4-isothiazolin-3-one, 2-bromo-2-nitropropane-1,3-diol and salicylic acid derivatives.

The previously mentioned solid vehicles, liquid vehicles, binders, thickeners, surfactants, anti-freezing agents and preservatives can each be used alone or in a suitable combination thereof corresponding to the purpose of use and the like.

Although the incorporated ratio of the compound of formula (I) of the present invention with respect to the total herbicide composition of the present invention can be increased or decreased as necessary and there are no particular limitations thereon, it is normally about 0.01% by weight to 90% by weight, and for example, in the case of being in the form of a dustable powder or granules, is preferably about 0.1% by weight to 50% by weight and more preferably about 0.5% by weight to 10% by weight, while in the case of being in the form of an emulsifiable concentrate, wettable powder or water dispersible granules, is preferably about 0.1% by weight to 90% by weight and more preferably about 0.5% by weight to 50% by weight.

These preparations can be provided for use in various types of applications by diluting to a suitable concentration as necessary followed by spraying or applying directly to plant foliage, soil or the surface of a rice paddy and the like.

The following provides an explanation of the present invention through examples thereof.

EXAMPLES

Example 1

Method for the Synthesis of 1-(3-chloro-4,5,6,7-tetrahydropyrazolo[1,5-a]pyridin-2-yl)-5-(cy clopropylmethylamino)pyrazole-4-carbonitrile (Compound 1)

5-amino-1-(3-chloro-4,5,6,7-tetrahydropyrazolo[1,5-a]pyridin-2-yl)pyrazole-4-carbonitrile (100 g) was dissolved in N,N-dimethylformamide (400 ml) followed by the addition of sodium hydroxide (16.8 g) and tetrabutyl ammonium bromide (catalytic amount) and stirring. Chloromethylcyclopropane (37.9 g) was then slowly dropped therein followed by reacting for 2 hours at 50° C. Following completion of the reaction, water was added and the precipitated solid was washed with ethyl acetate to obtain the desired compound (75 g).

Example 2

Method for the Synthesis of N-(1-(3-chloro-4,5,6,7-tetrahydropyrazolo[1,5-a]pyridin-2-yl)-4-cyanopyrazol-5-yl)-N-(cyclopropylmethyl)-2,2,2-trifluoroacetoamide (Compound 2)

1-(3-chloro-4,5,6,7-tetrahydropyrazolo[1,5-a]pyridin-2-yl)-5-(cy clopropylmethylamino)pyrazole-4-carbonitrile (3.5 g) was dissolved in acetonitrile (10 ml) and stirred followed by slowly dropping therein trifluoroacetic anhydride (11.6 g). After stirring for 1 day at 50° C., water was added to the reaction mixture followed by extraction with ethyl acetate. After drying with sodium sulfate, the solvent was distilled off under reduced pressure and the resulting crude product was purified by silica gel column chromatography (hexane/ethyl acetate=4:1) to obtain the desired compound (3.5 g).

Example 3

Method for the Synthesis of 1-(3-chloro-4,5,6,7-tetrahydropyrazolo[1,5-a]pyrazin-2-yl)-5-(cy clopropylmethylamino)pyrazole-4-carbonitrile (Alternative Method for the synthesis of Compound 1)

5-amino-1-(3-chloro-4,5,6,7-tetrahydropyrazolo[1,5-a]pyridin-2-yl)pyrazole-4-carbonitrile (5.3 g) was dissolved in acetonitrile (20 ml) and stirred followed by slowly dropping therein cyclopropanecarboxylic acid chloride (2.5 g) and refluxing for 3 hours. Following completion of the reaction, the temperature of the reaction mixture was lowered to room temperature followed by the addition of water and sequentially washing the precipitated solid with hexane and ethyl acetate to obtain N-(1-(3-chloro-4,5,6,7-tetrahydropyrazolo[1,5-a]pyridin-2-yl)-4-cyanopyrazol-5-yl)cyclopropane carboxamide (3.8 g).

N-(1-(3-chloro-4,5,6,7-tetrahydropyrazolo[1,5-a]pyridin-2-yl)-4-cyanopyrazol-5-yl)cyclopropane carboxamide (1.6 g) was dissolved in toluene (10 ml) followed by the addition of phosphorous pentachloride (1.25 g) and refluxing for 2 hours. After additionally adding phosphorous pentachloride (0.13 g), refluxing was further carried out for 1 hour followed by stirring for 1 day at room temperature. The reaction mixture was placed in ice water, extracted with chloroform and washed with 0.1 eq. aqueous sodium hydroxide solution followed by drying with sodium sulfate and concentrating under reduced pressure. After washing the resulting crude product with hexane, ethanol (10 ml) and sodium borohydride (190 mg) were added thereto and reacted for 1 day at room temperature. Following completion of the reaction, water was added followed by extraction with ethyl acetate, drying with sodium sulfate and distilling off the solvent under reduced pressure. The resulting crude product was purified by silica gel column chromatography (hexane/ethyl acetate=2:1) to obtain the desired compound (1.2 g).

Example 4

Method for the Synthesis of 1-(3-chloro-4,5,6,7-tetrahydropyrazolo[1,5-a]pyridin-2-yl)-5-(1-cyclopropylethylamino)pyrazole-4-carbonitrile (Compound 9)

5-amino-1-(3-chloro-4,5,6,7-tetrahydropyrazolo[1,5-a]pyridin-2-yl)pyrazole-4-carbonitrile (20 g) and p-toluenesulfonate monohydrate (4.34 g) were dissolved in toluene (100 ml) and stirred followed by adding cyclopropyl methyl ketone (31.9 g) and refluxing for 2 days. Water formed during the reaction was removed using a 4 A molecular sieve. Following completion of the reaction, the reaction mixture was filtered with Celite at 50° C. and washed with ethyl acetate followed by concentrating the mother liquid at an arbitrary ratio and purifying by silica gel column chromatography (hexane/ethyl acetate=1:2). Ethanol (200 ml) and sodium borohydride (5.8 g) were added to the resulting viscous compound and reacted for 1 day at room temperature. Following completion of the reaction, water was added to the reaction mixture followed by extraction with ethyl acetate, drying with sodium sulfate and distilling off the solvent under reduced pressure. The resulting crude product was purified by silica gel column chromatography (hexane/ethyl acetate=1:1) to obtain the desired compound (6.2 g).

Example 5

Method for the Synthesis of 1-(3-chloro-4,5,6,7-tetrahydropyrazolo[1,5-a]pyridin-2-yl)-5-(di cyclopropylmethylamino)pyrazole-4-carbonitrile (Compound 10)

5-amino-1-(3-chloro-4,5,6,7-tetrahydropyrazolo[1,5-a]pyridin-2-yl)pyrazole-4-carbonitrile (10 g) and p-toluenesulfonate monohydrate (2.2 g) were dissolved in toluene (50 ml) and stirred followed by adding cyclopropyl methyl ketone (8.8 g) and refluxing for 5.5 hours. Water formed during the reaction was removed using a 4 A molecular sieve. Following completion of the reaction, the reaction mixture was filtered with Celite at 50° C. and washed with ethyl acetate followed by distilling off the solvent under reduced pressure. Ethanol (40 ml) and sodium borohydride (1.5 g) were added to the resulting compound and reacted for 1 day at room temperature. Following completion of the reaction, water was added to the reaction mixture followed by extraction with ethyl acetate, drying with sodium sulfate and concentrating the solvent under reduced pressure. The resulting crude product was purified by silica gel column chromatography (hexane/ethyl acetate=1:1) to obtain the desired compound (2.1 g).

Example 6

Method for the Synthesis of 1-(3-chloro-4,5,6,7-tetrahydropyrazolo[1,5-a]pyridin-2-yl)-5-(1-methyl-cyclopropyl)methylamino)pyrazole-4-carbonitrile (Compound 4)

5-amino-1-(3-chloro-4,5,6,7-tetrahydropyrazolo[1,5-a]pyridin-2-yl)pyrazole-4-carbonitrile (64.5 g) was dissolved in N,N-dimethylformamide (250 ml) followed by the addition of sodium hydroxide (24.5 g) and tetrabutyl ammonium chloride (1.8 g) and stirring. 1-(bromomethyl)-1-methylcyclopropane (44.0 g) was slowly dropped therein and reacted for 2 hours at 70° C. Following completion of the reaction, water was added followed by extraction with ethyl acetate, drying with sodium sulfate and distilling off the solvent under reduced pressure. The resulting crude product was purified by silica gel column chromatography (hexane/ethyl acetate=1:1) to obtain the desired compound (50 g).

Example 7

Method for the Synthesis of 1-(bromomethyl)-1-methylcyclopropane Used in Above Reaction 1-methylcyclopropane carboxylic acid (100 g) was dissolved in tetrahydrofuran (1.31 l) and stirred followed by adding sodium borohydride (34 g) in several additions a little at a time. Boron trifluoride diethyl ether complex (170 g) was slowly dropped therein followed by stirring for 3 days at room temperature. Three days later, the reaction mixture was poured into ice water, and after filtering out the precipitated solid, the tetrahydrofuran was distilled off under reduced pressure followed by extraction with dichloromethane and drying with sodium sulfate. After drying, the solvent was distilled off under reduced pressure to obtain (1-methylcyclopropyl)methanol (70 g).

(1-methylcyclopropyl)methanol (70 g) was dissolved in dichloromethane (1.51 l) and stirred. Carbon tetrabromide (371 g) was then added thereto, the reaction mixture was cooled with an ice bath and triphenylphosphine (294 g) dissolved in methylene chloride (500 ml) was slowly dropped in followed by reacting for 2 days at room temperature. Following completion of the reaction, the solvent was distilled off and N,N-dimethylformamide (300 ml) was added followed by distilling off under reduced pressure to obtain the desired compound (72 g).

The starting material in the form of the compound of formula (II) was synthesized in accordance with WO 93/10100 and WO 94/08999.

The examples listed in the following tables can be synthesized by the same manner as the above-mentioned methods or obtained in the same manner as the above-mentioned methods.

TABLE 1

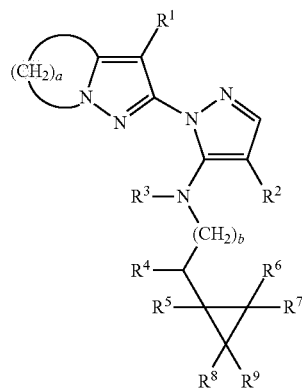

| Compound | R¹ | R² | R³ | R⁴ | R⁵ | R⁶ | R⁷ | R⁸ | R⁹ | a | b | mp | Refrative index (° C.) |
|---|---|---|---|---|---|---|---|---|---|---|---|---|---|
| 1 | Cl | CN | H | H | H | H | H | H | H | 4 | 0 | 165-166 | |
| 2 | Cl | CN | COCF₃ | H | H | H | H | H | H | 4 | 0 | 87.3-101 | |
| 3 | Cl | CN | COC₂F₅ | H | H | H | H | H | H | 4 | 0 | | 1.495(17.8) |
| 4 | Cl | CN | H | H | Me | H | H | H | H | 4 | 0 | 137-142 | |
| 5 | Cl | CN | H | H | H | H | H | H | H | 3 | 0 | 171-174 | |
| 6 | Cl | CN | COCF₃ | H | H | H | H | H | H | 3 | 0 | 116-126 | |
| 7 | Cl | CN | H | H | Me | Cl | Cl | H | H | 4 | 0 | 157-159 | |
| 8 | Cl | CN | H | Me | Me | H | H | H | H | 4 | 0 | 109-114 | |
| 9 | Cl | CN | H | Me | H | H | H | H | H | 4 | 0 | 104-108 | |
| 10 | Cl | CN | H | c-propyl | H | H | H | H | H | 4 | 0 | 132-133 | |
| 11 | Cl | CN | H | phenyl | H | H | H | H | H | 4 | 0 | 193-196 | |
| 12 | Cl | CN | H | H | H | Me | H | H | H | 4 | 0 | 125-131 | |
| 13 | Cl | CN | COCF₃ | H | H | Me | H | H | H | 4 | 0 | | 1.523 (21.5) |
| 14 | Cl | CN | COCF₃ | Me | H | H | H | H | H | 4 | 0 | Semi-solid | |
| 15 | Cl | CN | H | p-chlorophenyl | H | H | H | H | H | 4 | 0 | Semi-solid | |
| 16 | Cl | CN | H | p-fluorophenyl | H | H | H | H | H | 4 | 0 | Semi-solid | |
| 17 | Cl | CN | COCF₃ | H | Me | Cl | Cl | H | H | 4 | 0 | 93.6-107 | |
| 18 | Cl | CN | H | H | Me | H | H | H | H | 3 | 0 | 134-139 | |
| 19 | Cl | CN | H | H | H | Me | H | H | H | 3 | 0 | 112-117 | |
| 20 | Cl | CN | COCF₃ | H | Me | H | H | H | H | 3 | 0 | | |
| 21 | Cl | CN | COCF₃ | H | H | Me | H | H | H | 3 | 0 | | |
| 22 | Cl | CN | H | Et | H | H | H | H | H | 4 | 0 | | |
| 23 | Cl | CN | COCF₃ | Et | H | H | H | H | H | 4 | 0 | | |
| 24 | Cl | CN | H | n-Pro | H | H | H | H | H | 4 | 0 | | |
| 25 | Cl | CN | COCF₃ | n-Pro | H | H | H | H | H | 4 | 0 | | |
| 26 | Cl | CN | H | i-Pro | H | H | H | H | H | 4 | 0 | | |
| 27 | Cl | CN | COCF₃ | i-Pro | H | H | H | H | H | 4 | 0 | | |
| 28 | Cl | CN | H | n-Butyl | H | H | H | H | H | 4 | 0 | | |
| 29 | Cl | CN | COCF₃ | n-Butyl | H | H | H | H | H | 4 | 0 | | |
| 30 | Cl | CN | H | n-pentyl | H | H | H | H | H | 4 | 0 | | |
| 31 | Cl | CN | COCF₃ | n-pentyl | H | H | H | H | H | 4 | 0 | | |
| 32 | Cl | CN | H | n-hexyl | H | H | H | H | H | 4 | 0 | | |
| 33 | Cl | CN | COCF₃ | n-hexyl | H | H | H | H | H | 4 | 0 | | |
| 34 | Cl | CN | H | H | H | Me | Me | 2-methyl-1-propenyl | H | 4 | 0 | | |
| 35 | Cl | CN | H | H | H | Me | Me | Me | Me | 4 | 0 | | |
| 36 | Cl | CN | H | H | H | Me | Me | H | H | 4 | 0 | 81.8 | |
| 37 | Cl | CN | COCF₃ | H | H | Me | Me | H | H | 4 | 0 | | |
| 38 | Cl | CN | COCF₃ | phenyl | H | H | H | H | H | 4 | 0 | | |
| 39 | Cl | CN | H | H | H | phenyl | H | H | H | 4 | 0 | | |
| 40 | Cl | CN | H | H | c-propyl | H | H | H | H | 4 | 0 | | |
| 41 | Cl | CN | H | H | H | c-propyl | H | H | H | 4 | 0 | | |
| 42 | Cl | CN | COC₃F₇ | H | H | H | H | H | H | 4 | 0 | | |
| 43 | Cl | CN | H | H | CF₃ | H | H | H | H | 4 | 0 | | |
| 44 | Cl | CN | COCF₃ | H | CF₃ | H | H | H | H | 4 | 0 | | |
| 45 | Cl | CN | H | c-butyl | H | H | H | H | H | 4 | 0 | | |
| 46 | Cl | CN | H | c-hexyl | H | H | H | H | H | 4 | 0 | | |
| 47 | Cl | CN | H | o-chlorophenyl | H | H | H | H | H | 4 | 0 | | |
| 48 | Cl | CN | H | o-fluorophenyl | H | H | H | H | H | 4 | 0 | | |
| 49 | Cl | CN | H | phenyl | H | H | H | H | H | 4 | 0 | | |
| 50 | Cl | CN | COCF₃ | H | phenyl | H | H | H | H | 4 | 0 | | |
| 51 | Cl | CN | H | H | o-tolyl | H | H | H | H | 4 | 0 | | |
| 52 | Cl | CN | COCF₃ | H | o-tolyl | H | H | H | H | 4 | 0 | | |
| 53 | Cl | CN | H | H | p-tolyl | H | H | H | H | 4 | 0 | | |
| 54 | Cl | CN | COCF₃ | H | p-tolyl | H | H | H | H | 4 | 0 | | |
| 55 | Cl | CN | H | H | H | H | H | H | H | 4 | 1 | 166-167 | |
| 56 | Cl | CN | COCF₃ | H | H | H | H | H | H | 4 | 1 | Semi-solid | |
| 57 | Cl | CN | COC₂F₅ | H | H | H | H | H | H | 4 | 1 | | |
| 58 | Cl | CN | H | H | Me | H | H | H | H | 4 | 1 | | |

TABLE 1-continued

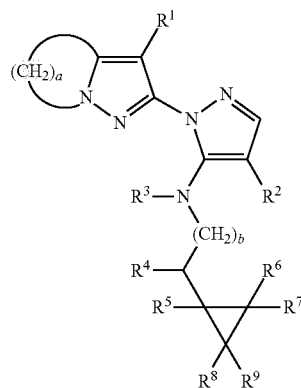

| Compound | R¹ | R² | R³ | R⁴ | R⁵ | R⁶ | R⁷ | R⁸ | R⁹ | a | b | mp | Refrative index (° C.) |
|---|---|---|---|---|---|---|---|---|---|---|---|---|---|
| 59 | Cl | CN | H | H | H | H | H | H | H | 3 | 1 | 150 | |
| 60 | Cl | CN | COCF₃ | H | H | H | H | H | H | 3 | 1 | Semi-solid | |
| 61 | Cl | CN | H | H | H | Cl | Cl | H | H | 4 | 1 | | |
| 62 | Cl | CN | H | Me | Me | H | H | H | H | 4 | 1 | | |
| 63 | Cl | CN | H | Me | H | H | H | H | H | 4 | 1 | | |
| 64 | Cl | CN | H | H | c-propyl | H | H | H | H | 4 | 1 | | |
| 65 | Cl | CN | H | H | phenyl | H | H | H | H | 4 | 1 | | |
| 66 | Cl | CN | H | H | H | Me | H | H | H | 4 | 1 | | |
| 67 | Cl | CN | COCF₃ | H | H | Me | H | H | H | 4 | 1 | | |
| 68 | Cl | CN | COCF₃ | Me | H | H | H | H | H | 4 | 1 | | |
| 69 | Cl | CN | H | H | p-chlorophenyl | H | H | H | H | 4 | 1 | | |
| 70 | Cl | CN | H | H | p-fluorophenyl | H | H | H | H | 4 | 1 | | |
| 71 | Cl | CN | COCF₃ | H | H | Cl | Cl | H | H | 4 | 1 | | |
| 72 | Cl | CN | H | H | H | H | H | H | H | 4 | 2 | | |
| 73 | Cl | CN | COCF₃ | H | H | H | H | H | H | 4 | 2 | | |
| 74 | Cl | CN | COC₂F₅ | H | H | H | H | H | H | 4 | 2 | | |
| 75 | Cl | CN | H | H | Me | H | H | H | H | 4 | 2 | | |
| 76 | Cl | CN | H | H | H | H | H | H | H | 3 | 2 | | |
| 77 | Cl | CN | COCF₃ | H | H | H | H | H | H | 3 | 2 | | |
| 78 | Cl | CN | H | H | H | Cl | Cl | H | H | 4 | 2 | | |
| 79 | Cl | CN | H | Me | Me | H | H | H | H | 4 | 2 | | |
| 80 | Cl | CN | H | Me | H | H | H | H | H | 4 | 2 | | |
| 81 | Cl | CN | H | H | c-propyl | H | H | H | H | 4 | 2 | | |
| 82 | Cl | CN | H | H | phenyl | H | H | H | H | 4 | 2 | | |
| 83 | Cl | CN | H | H | H | Me | H | H | H | 4 | 2 | | |
| 84 | Cl | CN | COCF₃ | H | H | Me | H | H | H | 4 | 2 | | |
| 85 | Cl | CN | COCF₃ | Me | H | H | H | H | H | 4 | 2 | | |
| 86 | Cl | CN | H | H | p-chlorophenyl | H | H | H | H | 4 | 2 | | |
| 87 | Cl | CN | H | H | p-fluorophenyl | H | H | H | H | 4 | 2 | | |
| 88 | Cl | CN | COCF₃ | H | H | Cl | Cl | H | H | 4 | 2 | | |
| 89 | Cl | CN | COC₂F₅ | H | H | H | H | H | H | 3 | 0 | | |
| 90 | Cl | CN | H | H | H | Cl | Cl | H | H | 3 | 0 | | |
| 91 | Cl | CN | H | Me | Me | H | H | H | H | 3 | 0 | | |
| 92 | Cl | CN | H | Me | H | H | H | H | H | 3 | 0 | | |
| 93 | Cl | CN | H | H | c-propyl | H | H | H | H | 3 | 0 | | |
| 94 | Cl | CN | H | H | phenyl | H | H | H | H | 3 | 0 | | |
| 95 | Cl | CN | COCF₃ | Me | H | H | H | H | H | 3 | 0 | | |
| 96 | Cl | CN | H | H | p-chlorophenyl | H | H | H | H | 3 | 0 | | |
| 97 | Cl | CN | H | H | p-fluorophenyl | H | H | H | H | 3 | 0 | | |
| 98 | Cl | CN | COCF₃ | H | H | Cl | Cl | H | H | 3 | 0 | | |
| 99 | Cl | CN | COCF₃ | H | H | H | H | H | H | 5 | 0 | | |
| 100 | Cl | CN | COC₂F₅ | H | H | H | H | H | H | 5 | 0 | | |
| 101 | Cl | CN | H | H | Me | H | H | H | H | 5 | 0 | | |
| 102 | Cl | CN | H | H | H | Cl | Cl | H | H | 5 | 0 | | |
| 103 | Cl | CN | H | Me | Me | H | H | H | H | 5 | 0 | | |
| 104 | Cl | CN | H | Me | H | H | H | H | H | 5 | 0 | | |
| 105 | Cl | CN | H | H | c-propyl | H | H | H | H | 5 | 0 | | |
| 106 | Cl | CN | H | H | phenyl | H | H | H | H | 5 | 0 | | |
| 107 | Cl | CN | H | H | H | Me | H | H | H | 5 | 0 | | |
| 108 | Cl | CN | COCF₃ | H | H | Me | H | H | H | 5 | 0 | | |
| 109 | Cl | CN | COCF₃ | Me | H | H | H | H | H | 5 | 0 | | |
| 110 | Cl | CN | H | H | p-chlorophenyl | H | H | H | H | 5 | 0 | | |
| 111 | Cl | CN | H | H | p-fluorophenyl | H | H | H | H | 5 | 0 | | |
| 112 | Cl | CN | COCF₃ | H | H | Cl | Cl | H | H | 5 | 0 | | |
| 113 | Cl | CN | H | c-propyl | H | H | H | H | H | 3 | 0 | | |
| 114 | Cl | NO₂ | H | H | H | H | H | H | H | 4 | 0 | 140 | |
| 115 | Cl | NO₂ | COCF₃ | H | H | H | H | H | H | 4 | 0 | | 1.508 (25.5) |
| 116 | Cl | NO₂ | COC₃F₇ | H | H | H | H | H | H | 4 | 0 | | |

TABLE 1-continued

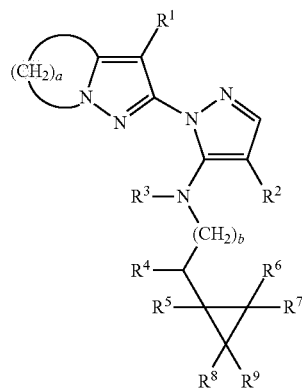

| Compound | R¹ | R² | R³ | R⁴ | R⁵ | R⁶ | R⁷ | R⁸ | R⁹ | a | b | mp | Refrative index (° C.) |
|---|---|---|---|---|---|---|---|---|---|---|---|---|---|
| 117 | Cl | $NO_2$ | H | Et | H | H | H | H | H | 4 | 0 | | |
| 118 | Cl | $NO_2$ | $COCF_3$ | Et | H | H | H | H | H | 4 | 0 | | |
| 119 | Cl | $NO_2$ | H | n-Pro | H | H | H | H | H | 4 | 0 | | |
| 120 | Cl | $NO_2$ | $COCF_3$ | n-Pro | H | H | H | H | H | 4 | 0 | | |
| 121 | Cl | $NO_2$ | H | i-Pro | H | H | H | H | H | 4 | 0 | | |
| 122 | Cl | $NO_2$ | $COCF_3$ | i-Pro | H | H | H | H | H | 4 | 0 | | |
| 123 | Cl | $NO_2$ | H | n-Butyl | H | H | H | H | H | 4 | 0 | | |
| 124 | Cl | $NO_2$ | $COCF_3$ | n-Butyl | H | H | H | H | H | 4 | 0 | | |
| 125 | Cl | $NO_2$ | H | n-pentyl | H | H | H | H | H | 4 | 0 | | |
| 126 | Cl | $NO_2$ | $COCF_3$ | n-pentyl | H | H | H | H | H | 4 | 0 | | |
| 127 | Cl | $NO_2$ | H | n-hexyl | H | H | H | H | H | 4 | 0 | | |
| 128 | Cl | $NO_2$ | $COCF_3$ | n-hexyl | H | H | H | H | H | 4 | 0 | | |
| 129 | Cl | $NO_2$ | H | H | H | Me | Me | 2-methyl-1-propenyl | H | 4 | 0 | | |
| 130 | Cl | $NO_2$ | H | H | H | Me | Me | Me | Me | 4 | 0 | | |
| 131 | Cl | $NO_2$ | H | H | H | Me | Me | H | H | 4 | 0 | | 1.592 (20.3) |
| 132 | Cl | $NO_2$ | $COCF_3$ | H | H | Me | Me | H | H | 4 | 0 | | |
| 133 | Cl | $NO_2$ | H | phenyl | H | H | H | H | H | 4 | 0 | | |
| 134 | Cl | $NO_2$ | $COCF_3$ | phenyl | H | H | H | H | H | 4 | 0 | | |
| 135 | Cl | $NO_2$ | H | H | H | H | H | H | H | 4 | 1 | 86.9-87.7 | |
| 136 | Cl | $NO_2$ | $COCF_3$ | H | H | H | H | H | H | 4 | 1 | | 1.537 (21.1) |
| 137 | Cl | $NO_2$ | H | H | H | H | H | H | H | 4 | 2 | | |
| 138 | Cl | $NO_2$ | $COCF_3$ | H | H | H | H | H | H | 4 | 2 | | |
| 139 | Cl | $NO_2$ | H | H | H | H | H | H | H | 3 | 0 | | |
| 140 | Cl | $NO_2$ | $COCF_3$ | H | H | H | H | H | H | 3 | 0 | | |
| 141 | Cl | $NO_2$ | H | H | H | H | H | H | H | 5 | 0 | | |
| 142 | Cl | $NO_2$ | $COCF_3$ | H | H | H | H | H | H | 5 | 0 | | |
| 143 | Cl | Br | H | H | H | H | H | H | H | 4 | 0 | | |
| 144 | Cl | Br | $COCF_3$ | H | H | H | H | H | H | 4 | 0 | | |
| 145 | Cl | Cl | H | H | H | H | H | H | H | 4 | 0 | 96.6-97.2 | |
| 146 | Cl | Cl | $COCF_3$ | H | H | H | H | H | H | 4 | 0 | | |
| 147 | Br | CN | H | H | H | H | H | H | H | 4 | 0 | 136-137 | |
| 148 | Br | CN | $COCF_3$ | H | H | H | H | H | H | 4 | 0 | 98-99 | |
| 149 | Br | CN | $COC_3F_7$ | H | H | H | H | H | H | 4 | 0 | | |
| 150 | Br | CN | H | H | H | H | H | H | H | 4 | 1 | | |
| 151 | Br | CN | $COCF_3$ | H | H | H | H | H | H | 4 | 1 | | |
| 152 | Br | CN | H | H | H | H | H | H | H | 4 | 2 | | |
| 153 | Br | CN | $COCF_3$ | H | H | H | H | H | H | 4 | 2 | | |
| 154 | Br | CN | H | H | H | H | H | H | H | 3 | 0 | | |
| 155 | Br | CN | $COCF_3$ | H | H | H | H | H | H | 3 | 0 | | |
| 156 | Br | CN | H | H | H | H | H | H | H | 5 | 0 | | |
| 157 | Br | CN | $COCF_3$ | H | H | H | H | H | H | 5 | 0 | | |
| 158 | Br | $NO_2$ | H | H | H | H | H | H | H | 4 | 0 | 127-128 | |
| 159 | Br | $NO_2$ | $COCF_3$ | H | H | H | H | H | H | 4 | 0 | 86-87 | |
| 160 | Br | $NO_2$ | H | H | H | H | H | H | H | 4 | 1 | | |
| 161 | Br | $NO_2$ | $COCF_3$ | H | H | H | H | H | H | 4 | 1 | | |
| 162 | Br | $NO_2$ | H | H | H | H | H | H | H | 4 | 1 | | |
| 163 | Br | $NO_2$ | $COCF_3$ | H | H | H | H | H | H | 4 | 1 | | |
| 164 | Br | $NO_2$ | H | H | H | H | H | H | H | 4 | 2 | | |
| 165 | Br | $NO_2$ | $COCF_3$ | H | H | H | H | H | H | 4 | 2 | | |
| 166 | Br | $NO_2$ | H | H | H | H | H | H | H | 3 | 0 | | |
| 167 | Br | $NO_2$ | $COCF_3$ | H | H | H | H | H | H | 3 | 0 | | |
| 168 | Br | $NO_2$ | H | H | H | H | H | H | H | 5 | 0 | | |
| 169 | Br | $NO_2$ | $COCF_3$ | H | H | H | H | H | H | 5 | 0 | | |
| 170 | Cl | $NO_2$ | H | Me | H | H | H | H | H | 4 | 0 | | |
| 171 | Cl | $NO_2$ | H | H | c-propyl | H | H | H | H | 4 | 0 | | |
| 172 | Cl | $NO_2$ | H | H | H | Me | H | H | H | 4 | 0 | 100-106 | |
| 173 | Cl | $NO_2$ | $COCF_3$ | Me | H | H | H | H | H | 4 | 0 | | |
| 174 | Cl | $NO_2$ | $COCF_3$ | H | H | Me | H | H | H | 4 | 0 | | |

TABLE 1-continued

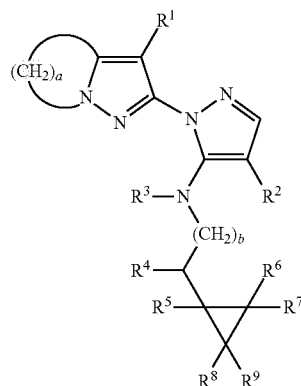

| Compound | R¹ | R² | R³ | R⁴ | R⁵ | R⁶ | R⁷ | R⁸ | R⁹ | a | b | mp | Refrative index (° C.) |
|---|---|---|---|---|---|---|---|---|---|---|---|---|---|
| 175 | Br | NO₂ | H | Me | H | H | H | H | H | 4 | 0 | | |
| 176 | Br | NO₂ | H | H | c-propyl | H | H | H | H | 4 | 0 | | |
| 177 | Br | NO₂ | H | H | H | Me | H | H | H | 4 | 0 | 104-108 | |
| 178 | Br | NO₂ | COCF₃ | Me | H | H | H | H | H | 4 | 0 | | |
| 179 | Br | NO₂ | COCF₃ | H | H | Me | H | H | H | 4 | 0 | | |
| 180 | Br | CN | H | Me | H | H | H | H | H | 4 | 0 | | |
| 181 | Br | CN | H | H | c-propyl | H | H | H | H | 4 | 0 | | |
| 182 | Br | CN | H | H | H | Me | H | H | H | 4 | 0 | 122-126 | |
| 183 | Br | CN | COCF₃ | Me | H | H | H | H | H | 4 | 0 | | |
| 184 | Br | CN | COCF₃ | H | H | Me | H | H | H | 4 | 0 | | |
| 185 | Cl | CN | H | H | H | F | F | H | H | 4 | 0 | 123-125 | |
| 186 | Cl | CN | COCF₃ | H | H | F | F | H | H | 4 | 0 | 80-85 | |
| 187 | Cl | NO₂ | H | H | H | F | F | H | H | 4 | 0 | 110-112 | |
| 188 | Cl | NO₂ | COCF₃ | H | H | F | F | H | H | 4 | 0 | Semi-solid | |
| 189 | Br | CN | H | H | H | F | F | H | H | 4 | 0 | | |
| 190 | Br | CN | COCF₃ | H | H | F | F | H | H | 4 | 0 | | |
| 191 | Br | NO₂ | H | H | H | F | F | H | H | 4 | 0 | | |
| 192 | Br | NO₂ | COCF₃ | H | H | F | F | H | H | 4 | 0 | | |
| 193 | Cl | CN | H | H | H | F | F | F | F | 4 | 0 | | |
| 194 | Cl | CN | COCF₃ | H | H | F | F | F | F | 4 | 0 | | |
| 195 | Cl | NO₂ | H | H | H | F | F | F | F | 4 | 0 | | |
| 196 | Cl | NO₂ | COCF₃ | H | H | F | F | F | F | 4 | 0 | | |
| 197 | Br | CN | H | H | H | F | F | F | F | 4 | 0 | | |
| 198 | Br | CN | COCF₃ | H | H | F | F | F | F | 4 | 0 | | |
| 199 | Br | NO₂ | H | H | H | F | F | F | F | 4 | 0 | | |
| 200 | Br | NO₂ | COCF₃ | H | H | F | F | F | F | 4 | 0 | | |
| 201 | Cl | CN | H | H | F | H | H | H | H | 4 | 0 | | |
| 202 | Cl | CN | COCF₃ | H | F | H | H | H | H | 4 | 0 | | |
| 203 | Cl | NO₂ | H | H | F | H | H | H | H | 4 | 0 | | |
| 204 | Cl | NO₂ | COCF₃ | H | F | H | H | H | H | 4 | 0 | | |
| 205 | Br | CN | H | H | F | H | H | H | H | 4 | 0 | | |
| 206 | Br | CN | COCF₃ | H | F | H | H | H | H | 4 | 0 | | |
| 207 | Br | NO₂ | H | H | F | H | H | H | H | 4 | 0 | | |
| 208 | Br | NO₂ | COCF₃ | H | F | H | H | H | H | 4 | 0 | | |
| 209 | Cl | CN | H | H | Cl | H | H | H | H | 4 | 0 | | |
| 210 | Cl | CN | COCF₃ | H | Cl | H | H | H | H | 4 | 0 | | |
| 211 | Cl | NO₂ | H | H | Cl | H | H | H | H | 4 | 0 | | |
| 212 | Cl | NO₂ | COCF₃ | H | Cl | H | H | H | H | 4 | 0 | | |
| 213 | Br | CN | H | H | Cl | H | H | H | H | 4 | 0 | | |
| 214 | Br | CN | COCF₃ | H | Cl | H | H | H | H | 4 | 0 | | |
| 215 | Br | NO₂ | H | H | Cl | H | H | H | H | 4 | 0 | | |
| 216 | Br | NO₂ | COCF₃ | H | Cl | H | H | H | H | 4 | 0 | | |
| 217 | Cl | CN | H | H | Me | F | F | H | H | 4 | 0 | | |
| 218 | Cl | CN | COCF₃ | H | Me | F | F | H | H | 4 | 0 | | |
| 219 | Cl | NO₂ | H | H | Me | F | F | H | H | 4 | 0 | | |
| 220 | Cl | NO₂ | COCF₃ | H | Me | F | F | H | H | 4 | 0 | | |
| 221 | Br | CN | H | H | Me | F | F | H | H | 4 | 0 | | |
| 222 | Br | CN | COCF₃ | H | Me | F | F | H | H | 4 | 0 | | |
| 223 | Br | NO₂ | H | H | Me | F | F | H | H | 4 | 0 | | |
| 224 | Br | NO₂ | COCF₃ | H | Me | F | F | H | H | 4 | 0 | | |
| 225 | Cl | CN | COCF₃ | H | Me | H | H | H | H | 4 | 0 | | |
| 226 | Cl | NO₂ | H | H | Me | H | H | H | H | 4 | 0 | 112-115 | |
| 227 | Cl | NO₂ | COCF₃ | H | Me | H | H | H | H | 4 | 0 | | |
| 228 | Br | CN | H | H | Me | H | H | H | H | 4 | 0 | 133-135 | |
| 229 | Br | CN | COCF₃ | H | Me | H | H | H | H | 4 | 0 | | |
| 230 | Br | NO₂ | H | H | Me | H | H | H | H | 4 | 0 | 125-129 | |
| 231 | Br | NO₂ | COCF₃ | H | Me | H | H | H | H | 4 | 0 | | |

Preparation Examples

1. Dustable Powder

| | |
|---|---|
| Compound of formula (I) | 10 parts by weight |
| Talc | 90 parts by weight |

A dustable powder is obtained by mixing the above components and finely crushing with a hammer mill.

2. Wettable Powder

| | |
|---|---|
| Compound of formula (I) | 10 parts by weight |
| Polyoxyethylene alkyl aryl ether sulfate | 22.5 parts by weight |
| White carbon | 67.5 parts by weight |

A wettable powder is obtained by mixing the above components and finely crushing the mixture with a hammer mill.

3. Flowable Concentrate

| | |
|---|---|
| Compound of formula (I) | 10 parts by weight |
| Polyoxyethylene alkyl ether phosphate | 10 parts by weight |
| Bentonite | 5 parts by weight |
| Ethylene glycol | 5 parts by weight |
| Water | 70 parts by weight |

A flowable concentrate is obtained by mixing the above components and crushing using a wet pulverizer.

4. Emulsifiable Concentrate

| | |
|---|---|
| Compound of formula (I) | 15 parts by weight |
| Ethoxylated nonylphenol | 10 parts by weight |
| Cyclohexanone | 75 parts by weight |

An emulsifiable concentrate is obtained by mixing the above components.

5. Granules

| | |
|---|---|
| Compound of formula (I) | 5 parts by weight |
| Calcium lignin sulfonate | 3 parts by weight |
| Polycarboxylate | 3 parts by weight |
| Calcium carbonate | 89 parts by weight |

The above components are mixed followed by adding water, kneading, extruding and granulating. Subsequently, granules are obtained by drying followed by sizing.

Biological Testing Examples

1. Paddy Herbicidal Activity Test

Rice paddy soil was filled into a 1/10000 are pot followed by the addition of suitable amounts of water and chemical fertilizer, kneading, seeding with *Echinochloa crus-galli*, *Monochoria vaginalis* and *Scirpus juncoides* and maintaining in an irrigated state at a water depth of 3 cm.

Wettable powder of Target Compound (I) shown in Table 1 prepared in compliance with the preparation examples were diluted with a suitable amount of water, rice plants in the 2.0 leaf stage were transplanted during 3.5 leaf stage of *Echinochloa crus-galli*, and treated by dropping in chemical in the prescribed amount per are using a pipette.

After treating for 30 days in a glass greenhouse at an average atmospheric temperature of 30° C., the herbicidal efficacy thereof was investigated.

Evaluation of herbicidal efficacy was carried out by comparing growth inhibition rate (%) with an untreated group, while evaluation of phytotoxicity was carried out by comparing growth inhibition rate (%) with the state of a complete eradication group, and were evaluated at 11 levels indicated below.

```
0 (exponent): 0% to less than 10% (growth inhibition rate)
1: 10% to less than 20%
2: 20% to less than 30%
3: 30% to less than 40%
4: 40% to less than 50%
5: 50% to less than 60%
6: 60% to less than 70%
7: 70% to less than 80%
8: 80% to less than 90%
9: 90% to less than 100%
10: 100%
```

The results are shown in Table 2.

Control agent 4.84 (described in WO 94/08999)

[Chemical formula 6]

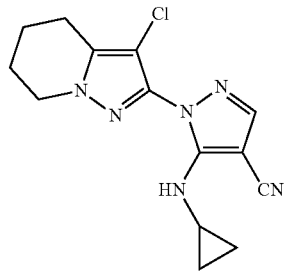

(4.84)

Control agent 4.129 (described in WO 94/08999)

[Chemical formula 7]

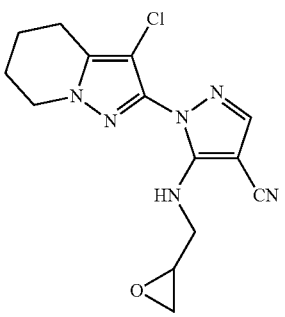

(4.129)

TABLE 2

| | 5g$^{a.i.}$/10a | | | | 1g$^{a.i.}$/10a | | | |
|---|---|---|---|---|---|---|---|---|
| Compound | Echinochloacrus-galli | Monochoria vaginalis | Scirpus juncoides | Rice plants | Echinochloacrus-galli | Monochoria vaginalis | Scirpus juncoides | Rice plants |
| 1 | 10 | 8 | 9 | 1 | 9 | 8 | 8 | 0 |
| 2 | 9 | 9 | 8 | 1 | 9 | 8 | 8 | 0 |
| 3 | 8 | 7 | 8 | 0 | 8 | 7 | 7 | 0 |
| 4 | 10 | 9 | 8 | 1 | 9 | 9 | 8 | 0 |
| 5 | 10 | 9 | 9 | 1 | 9 | 9 | 8 | 0 |
| 6 | 9 | 9 | 8 | 0 | 9 | 8 | 7 | 0 |
| 8 | 9 | 7 | 8 | 0 | 9 | 7 | 7 | 0 |
| 9 | 9 | 9 | 8 | 1 | 9 | 8 | 8 | 0 |
| 10 | 9 | 9 | 9 | 1 | 9 | 8 | 8 | 0 |
| 12 | 10 | 9 | 9 | 1 | 9 | 8 | 9 | 0 |
| 13 | 9 | 8 | 8 | 1 | 9 | 8 | 8 | 0 |
| 14 | 9 | 7 | 8 | 0 | 8 | 7 | 7 | 0 |
| 114 | 9 | 8 | 9 | 0 | 9 | 7 | 8 | 0 |
| 115 | 9 | 8 | 8 | 1 | 8 | 8 | 9 | 0 |
| 147 | 9 | 8 | 9 | 0 | 8 | 7 | 7 | 0 |
| 148 | 10 | 9 | 9 | 0 | 8 | 7 | 7 | 0 |
| 158 | 9 | 7 | 9 | 0 | 8 | 7 | 8 | 0 |
| 159 | 9 | 8 | 8 | 0 | 8 | 7 | 7 | 0 |
| 185 | 10 | 9 | 10 | 1 | 10 | 9 | 10 | 0 |
| 186 | 10 | 9 | 10 | 1 | 10 | 9 | 9 | 0 |
| 4.84 | 5 | 3 | 4 | 2 | 3 | 2 | 3 | 0 |
| 4.129 | 3 | 0 | 4 | 2 | 1 | 0 | 3 | 1 |

2. Farming Soil Treatment Test

Field soil was filled into a 1/6000 are pot followed by seeding with *Digitaria ciliaris*, *Chenopodium album* and *Amaranthus retroflexus* and covering with soil.

Wettable powder of compounds of formula (I) shown in Table 1 prepared in compliance with the preparation examples were diluted with water to the prescribed amount of chemical and uniformly sprayed onto each soil surface layer using 10 liters of sprayed water per are prior to weed growth following seeding.

After treating for 30 days in a glass greenhouse at an average atmospheric temperature of 30° C., the herbicidal efficacy thereof was investigated.

Evaluation of herbicidal efficacy was carried out in the same manner as the above-mentioned Test Example 1.

The results are shown in Table 3.

3. Weed Foliar Treatment Test

Soil was filled into a 1/6000 are pot followed by seeding with *Digitaria ciliaris*, *Chenopodium album* and *Amaranthus retroflexus*, covering with soil, and cultivating in a glass greenhouse at an average atmospheric temperature of 25° C.

Wettable powder of Target Compound (I) shown in Table 1 prepared in compliance with the preparation examples were diluted with water to the prescribed amount of chemical and uniformly sprayed onto the weeds using 15 liters of sprayed water per are when *Digitaria ciliaris* had grown to the 1.0 to 2.0 leaf stage.

After treating for 3 weeks in a glass greenhouse at an average atmospheric temperature of 25° C., the herbicidal efficacy thereof was investigated, Evaluation of herbicidal efficacy was carried out in the same manner as the above-mentioned Test Example 1.

TABLE 3

| | 10g$^{a.i.}$/10a | | | 5g$^{a.i.}$/10a | | |
|---|---|---|---|---|---|---|
| Compound | Digitaria ciliaris | Chenopodium album | Amaranthus retroflexus | Digitaria ciliaris | Chenopodium album | Amaranthus retroflexus |
| 1 | 10 | 10 | 10 | 10 | 10 | 10 |
| 2 | 10 | 10 | 10 | 10 | 10 | 10 |
| 9 | 10 | 10 | 10 | 10 | 10 | 10 |
| 10 | 10 | 10 | 10 | 10 | 10 | 10 |
| 12 | 10 | 10 | 10 | 10 | 10 | 10 |
| 147 | 10 | 10 | 10 | 10 | 10 | 10 |
| 148 | 10 | 10 | 10 | 10 | 10 | 10 |
| 185 | 10 | 10 | 10 | 10 | 10 | 10 |
| 186 | 10 | 10 | 10 | 10 | 10 | 10 |
| 4.84 | 5 | 6 | 6 | 5 | 6 | 6 |
| 4.129 | 5 | 6 | 7 | 4 | 6 | 6 |

The results are shown in Table 4.

TABLE 4

| | 10g$^{a.i.}$/10a | | | 5g$^{a.i.}$/10a | | |
|---|---|---|---|---|---|---|
| Compound | Digitaria ciliaris | Chenopodium album | Amaranthus retroflexus | Digitaria ciliaris | Chenopodium album | Amaranthus retroflexus |
| 1 | 10 | 10 | 10 | 10 | 10 | 10 |
| 2 | 10 | 10 | 10 | 10 | 10 | 10 |
| 9 | 10 | 10 | 10 | 10 | 10 | 10 |
| 10 | 10 | 10 | 10 | 10 | 10 | 10 |
| 12 | 10 | 10 | 10 | 10 | 10 | 10 |
| 147 | 10 | 10 | 10 | 10 | 10 | 10 |
| 148 | 10 | 10 | 10 | 10 | 10 | 10 |
| 185 | 10 | 10 | 10 | 10 | 10 | 10 |
| 186 | 10 | 10 | 10 | 10 | 10 | 10 |
| 4.84 | 6 | 7 | 7 | 5 | 6 | 6 |
| 4.129 | 5 | 7 | 7 | 4 | 6 | 7 |

INDUSTRIAL APPLICABILITY

According to the present invention, the compound for formula (I) of the present invention is useful as a herbicide against harmful plants since it has superior herbicidal efficacy against undesirable plants.

The invention claimed is:

1. A compound represented by the following formula (I):

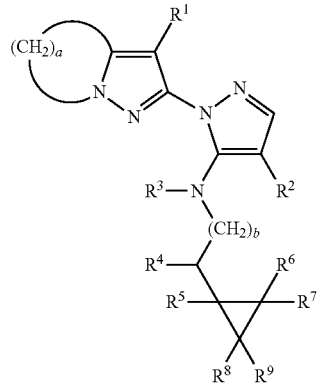

wherein
  $R^1$ represents a halogen atom,
  $R^2$ represents a cyano group, nitro group or halogen atom,
  $R^3$ represents a hydrogen atom, trifluoroacetyl group, pentafluoropropionyl group or heptafluorobutenyl group,
  $R^4$, $R^5$, $R^6$, $R^7$, $R^8$ and $R^9$ may be the same or different and represent (i) one or more hydrogen atoms, (ii) one or more halogen atoms, (iii) one or more $C_1$-$C_6$ alkyl groups optionally substituted with one or more halogen atoms, (iv) one or more $C_3$-$C_6$ cycloalkyl groups optionally substituted with one or more halogen atoms, (v) one or more $C_2$-$C_6$ alkenyl groups optionally substituted with one or more halogen atoms, (vi) one or more $C_2$-$C_6$ alkynyl groups optionally substituted with one or more halogen atoms, (vii) one or more $C_1$-$C_6$ alkoxy-$C_1$-$C_6$-alkyl groups optionally substituted with one or more halogen atoms, or (viii) one or more phenyl groups optionally substituted with one or more halogen atoms, nitro groups, cyano groups, $C_1$-$C_4$ alkyl groups optionally substituted with one or more halogen atoms, or $C_1$-$C_4$ alkoxy groups,
  a represents 3 to 5, and
  b represents 0 to 2.

2. The compound according to claim 1, wherein
  $R^1$ represents a chlorine atom or bromine atom,
  $R^4$, $R^5$, $R^6$, $R^7$, $R^8$ and $R^9$ may be the same or different and represent (i) one or more hydrogen atoms, (ii) one or more halogen atoms, (iii) one or more $C_1$-$C_4$ alkyl groups optionally substituted with one or more halogen atoms, (iv) one or more $C_3$-$C_6$ cycloalkyl groups optionally substituted with one or more halogen atoms, (v) one or more $C_2$-$C_4$ alkenyl groups optionally substituted with one or more halogen atoms, (vi) one or more $C_2$-$C_4$ alkynyl groups optionally substituted with one or more halogen atoms, (vii) one or more $C_1$-$C_4$ alkoxy-$C_2$-$C_4$-alkyl groups optionally substituted with one or more halogen atoms, or (viii) one or more phenyl groups optionally substituted with one or more halogen atoms, nitro groups, cyano groups, $C_1$-$C_4$ alkyl groups optionally substituted with one or more halogen atoms, or $C_1$-$C_4$ alkoxy groups, and
  a represents 4.

3. A method for synthesis of the compound according to claim 1, comprising the step of using, as a starting material, a compound represented by the following formula (II):

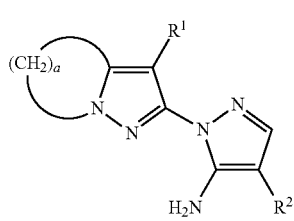

wherein,
  $R^1$ represents a halogen atom,
  $R^2$ represents a cyano group, nitro group or halogen atom, and
  a represents 3 to 5.

4. A herbicide composition comprising a herbicidally effective amount of at least one compound according to claim 1.

5. The herbicide composition according to claim 4, further comprising a formulation assistant.

6. A method for controlling undesirable plants, comprising a step of applying an effective amount of at least one compound according to claim 1 to an undesirable plant or to a location of an undesirable vegetation.

7. A herbicide composition comprising a herbicidally effective amount of at least one compound according to claim 2.

8. The herbicide composition according to claim 7, further comprising a formulation assistant.

9. A method for controlling undesirable plants, comprising a step of applying an effective amount of at least one compound according to claim 2 to an undesirable plant or to a location of an undesirable vegetation.

10. A method for controlling undesirable plants, comprising a step of applying an effective amount of the herbicide composition according to claim 4 to an undesirable plant or to a location of an undesirable vegetation.

11. A method for controlling undesirable plants, comprising a step of applying an effective amount of the herbicide composition according to claim 5 to an undesirable plant or to a location of an undesirable vegetation.

\* \* \* \* \*

UNITED STATES PATENT AND TRADEMARK OFFICE
CERTIFICATE OF CORRECTION

| | | |
|---|---|---|
| PATENT NO. | : 9,556,183 B2 | Page 1 of 1 |
| APPLICATION NO. | : 14/905007 | |
| DATED | : January 31, 2017 | |
| INVENTOR(S) | : Ken Matsubara et al. | |

It is certified that error appears in the above-identified patent and that said Letters Patent is hereby corrected as shown below:

Columns 25-26, in Table 2, the second row of the table, the third column of the table, "*Monochoria vaginalis*" should be replaced with --*Scirpus juncoides*--.

Columns 25-26, in Table 2, the second row of the table, the fourth column of the table, "*Scirpus juncoides*" should be replaced with --*Monochoria vaginalis*--.

Columns 25-26, in Table 2, the second row of the table, the seventh column of the table, "*Monochoria vaginalis*" should be replaced with --*Scirpus juncoides*--.

Columns 25-26, in Table 2, the second row of the table, the eighth column of the table, "*Scirpus juncoides*" should be replaced with --*Monochoria vaginalis*--.

Signed and Sealed this
Twelfth Day of September, 2017

Joseph Matal
*Performing the Functions and Duties of the*
*Under Secretary of Commerce for Intellectual Property and*
*Director of the United States Patent and Trademark Office*